United States Patent [19]

Meek, deceased et al.

[11] Plant 5,107

[45] Sep. 20, 1983

[54] CHRYSANTHEMUM PLANT

[75] Inventors: Jack M. Meek, deceased, late of Salinas, Calif.; by Saundra J. Meek, executrix, Canyon, Tex.; William E. Duffett, Salinas, Calif.

[73] Assignee: Yoder Brothers, Inc., Barberton, Ohio

[21] Appl. No.: 337,724

[22] Filed: Jan. 7, 1982

[51] Int. Cl.[3] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Koch

[57] ABSTRACT

A chrysanthemum plant known by the cultivar name Russet and particularly characterized as to uniqueness by the combined characteristics of flat capitulum form, with excellent form retention; anemone capitulum type; light yellow ray floret color; diameter across fact of capitulum ranging from 70 to 90 mm. at maturity; uniform eight week photoperiodic flowering response to short days; medium plant height when grown as a pinched spray pot, and spreading branching pattern.

3 Drawing Figures

The present invention comprises a new and distinct cultivar of *Chrysanthemum morifolium,* Ramat., hereinafter referred to by the cultivar name Russet.

Russet is a product of a planned breeding program which had the objective of creating new chrysanthemum cultivars for pinched spray pot mum programs having anemone capitulum type, yellow ray floret color, eight week flowering response and having the ability to produce commercially acceptable quality in year round programs. Such traits in combination were not present in previously available commercial cultivars.

Russet was originated from a cross made in a controlled breeding program in Salinas, Calif. in 1977. The female parent was an unnamed yellow anemone seedling originated by John Culbert and the University of Illinois (#73-99). The male parent of Russet was an unnamed color intensification mutant of the cultivar Fiesta, with Fiesta being disclosed in U.S. Plant Pat. No. 3,632.

Russet was discovered and selected as one flowering plant within the progeny of the stated cross by William E. Duffett on Nov. 9, 1978 in a controlled environment in Salinas, Calif.

The first act of asexual reproduction of Russet was accomplished when vegetative cuttings were taken from the initial selection in Feb., 1979 in a controlled environment in Salinas, Calif. by a technician working under formulations established and supervised by Jack M. Meek. Horticultural examination of selected units initiated Aug. 22, 1979 has demonstrated that the combination of characteristics as herein disclosed for Russet are firmly fixed and are retained through successive generations of asexual reproduction.

Russet has not been observed under all possible environmental conditions. The phenotype may vary significantly with variations in environment such as temperature, light intensity and day length. The observations, measurements and comparisons describe plants grown in Salinas, Calif. under greenhouse conditions which approximate those generally used in commercial practice.

The following traits have been repeatedly observed and are determined to be basic characteristics of Russet which in combintion distinguish this chrysanthemum as a new and distinct cultivar:

(1) flat capitulum form, with excellent form retention;

(2) anemone capitulum type;

(3) light yellow ray floret color;

(4) diameter across face of capitulum ranging from 70 to 90 mm. at maturity;

(5) uniform eight week photoperiodic flowering response to short days;

(6) medium plant height (requiring 1-2 long day weeks prior to pinch and short days, and one application 2500 ppm B-9 SP 14 to 21 days after the beginning of short days to attain a flowered plant height of 30 to 45 cm., and (7) spreading branching pattern.

The accompanying photographic drawings show typical inflorescence and foliage characteristics of Russet, with the colors being as nearly true as possible with illustrations of this type. Sheet 1 is a color photograph of a flowering plant of Russet. Sheet 2 is a black and white photograph showing three views of the inflorescence of Russet. Sheet 3 is a black and white photograph showing the foliage of Russet at three stages of growth.

Of the many commercial cultivars known to the present inventors, the most similar in comparison to Russet is Fiesta. Reference is made to attached Chart A which compares certain characteristics of Russet to those same characteristics of Fiesta.

When generally compared to Fiesta, Russet has different capitulum type, more spreading branching pattern and shorter plant height. The ray floret color, capitulum form, diameter across face of capitulum and flower response period of Russet are similar to those same characteristics of Fiesta.

In the flowering description, color references are made to The Royal Horticultural Colour Chart. The color values were determined between 2:00 and 2:30 P.M. on Sept. 8, 1981 under 150 foot-candle light intensity at Salinas, Calif.

Classification:

*Botanical.*—*Chrysanthemum morifolium,* Ramat. cv Russet.

*Commercial.*—Pinched spray pot.

INFLORESCENCE

A. Capitulum:
*Form.*—Flat.
*Type.*—Anemone.
*Diameter across face.*—70 to 90 mm.

B. Corolla of ray florets:
*General tonality from a distance of three meters*—Approximately 6D.
*Color (abaxial)*—12B (immature) oxidizing to 11C (mature).
*Color (adaxial).*—13D.

C. Corolla of disc florets:
*Shape.*—Elongated, typical anemone.
*Color (mature).*—Approximately 13B.
*Color (immature).*—Approximately 154B.

D. Reproductive organs
*Androecium.*—Present in disc florets only; scant to few; scant pollen.
*Gynoecium.*—Present in both ray and disc florets.

PLANT

A. General appearance:
*Height.*—Medium.
*Branching pattern.*—Spreading.

B. Foliage:
*Color (abaxial).*—Approximately 147A.
*Color (adaxial).*—Approximately 147B overlaid with white.

*Shape.*—Moderately lobed and serrated.

CHART A

COMPARISON OF RUSSET AND FIESTA

| CULTIVAR | RAY FLORET COLOR | CAPITULUM FORM AND TYPE | BRANCHING PATTERN |
|---|---|---|---|
| RUSSET | Light Yellow | Flat Anemone | Spreading |
| FIESTA | Light Yellow | Flat Daisy | Semi-Spreading |

| CULTIVAR | DIAMETER ACROSS FACE OF CAPITULUM | PLANT HEIGHT | FLOWERING RESPONSE PERIOD |
|---|---|---|---|
| RUSSET | 70 to 90 mm. | Medium | 8 Week |
| FIESTA | 70 to 85 mm. | Tall | 8 Week |

COMPARISONS MADE OF PLANTS GROWN AS PINCHED SPRAY POTS IN SALINAS, CALIFORNIA

We claim:

1. A new and distinct cultivar of *Chrysanthemum morifolium,* Ramat., plant known by the cultivar name of Russet, as described and illustrated, and particularly characterized as to uniqueness by the combined characteristics of flat capitulum form, with excellent form retention; anemone capitulum type; light yellow ray floret color; diameter across face of capitulum ranging from 70 to 90 mm. at maturity; uniform eight week flowering response; medium plant height, and spreading branching pattern.

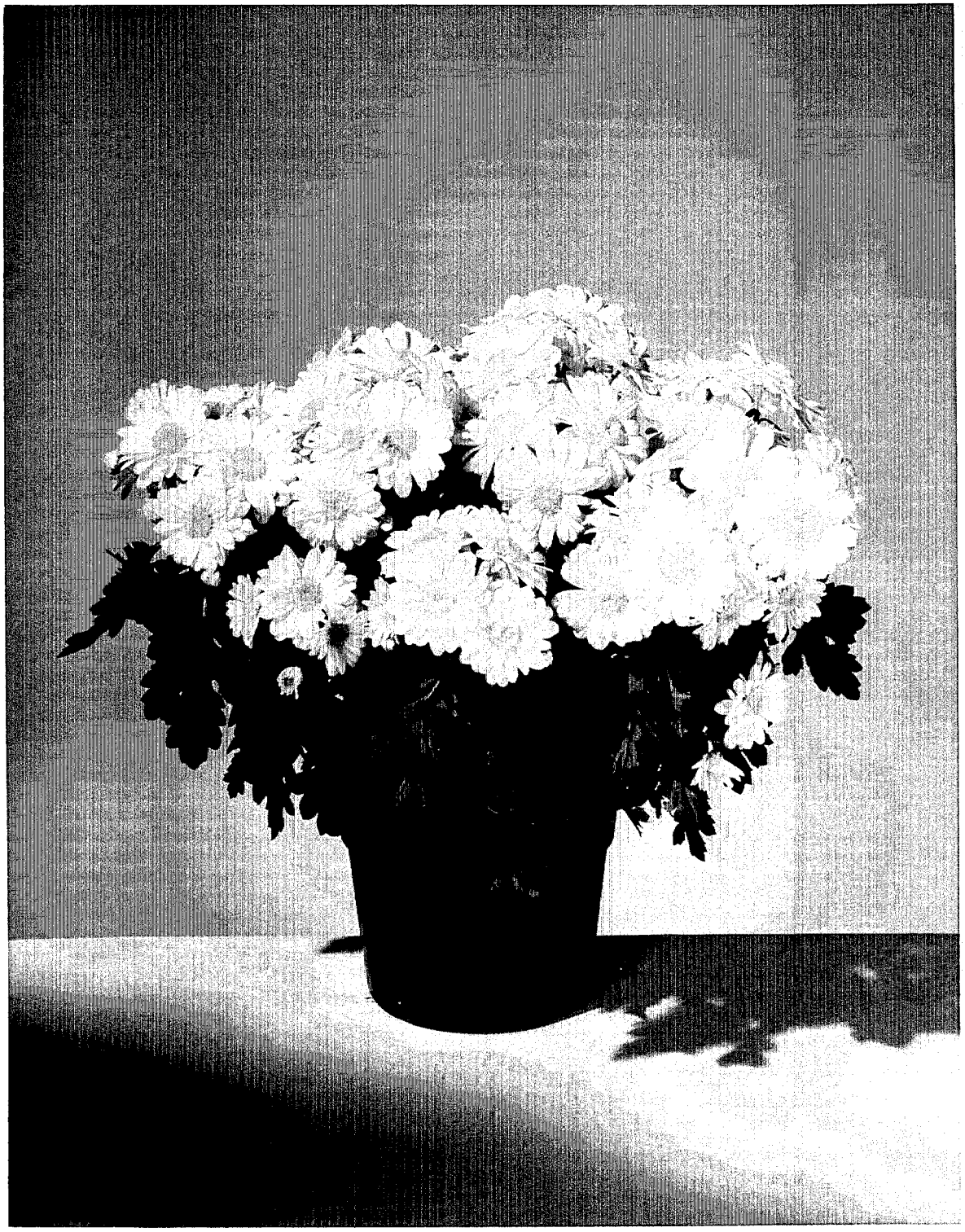

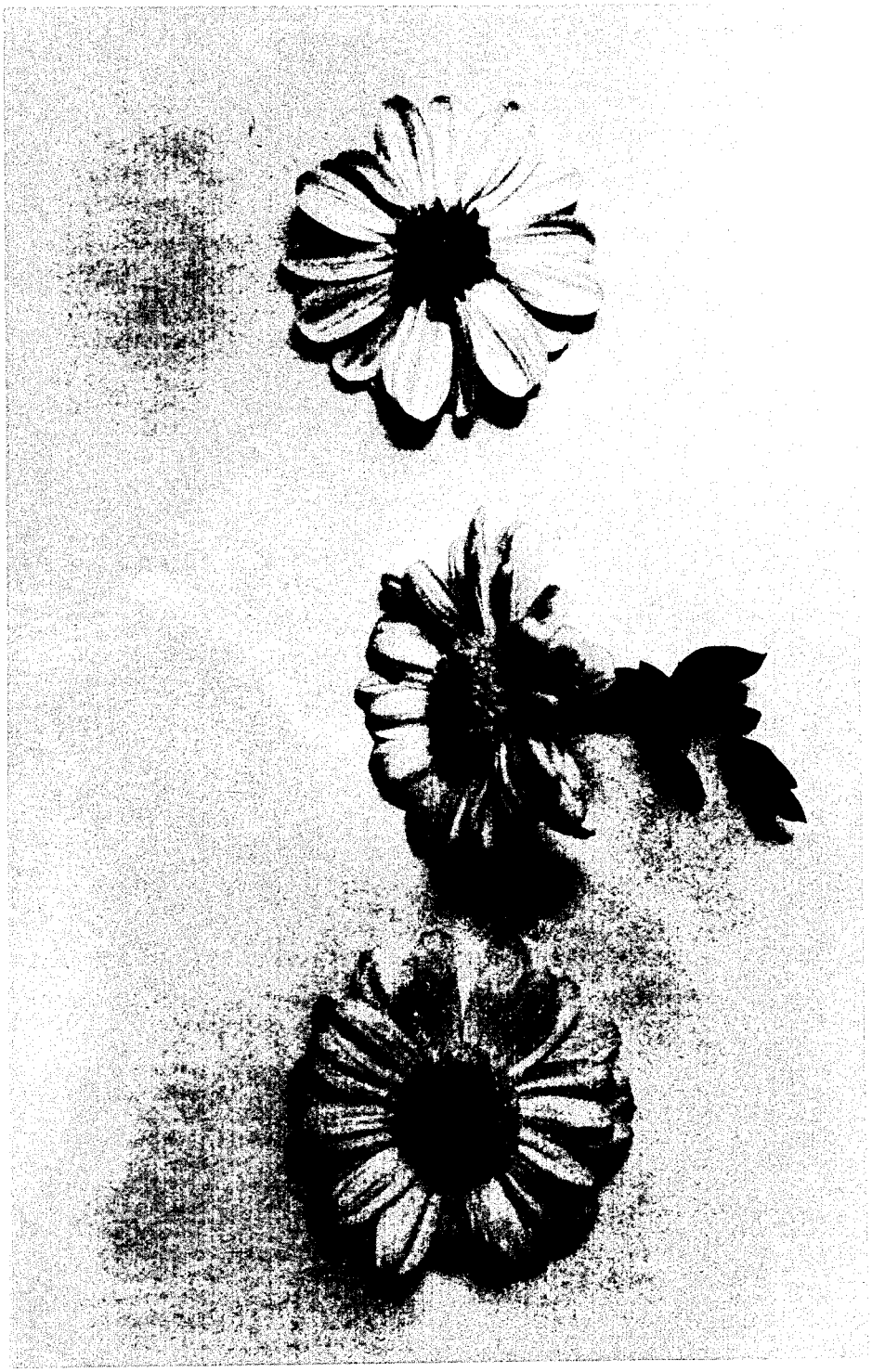

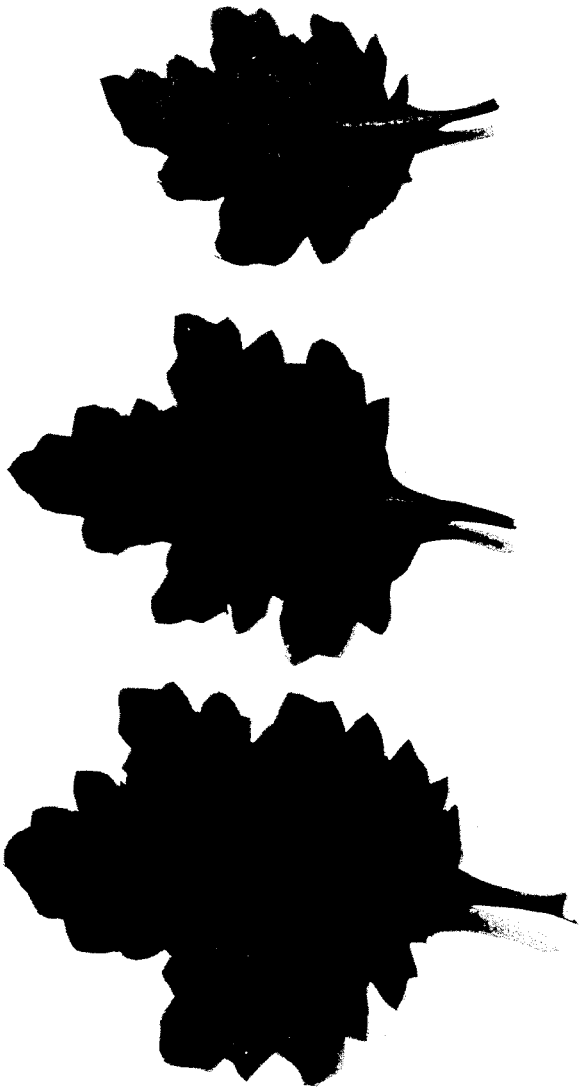

* * * * *